United States Patent [19]

Pfeifer

[11] Patent Number: 4,483,342

[45] Date of Patent: Nov. 20, 1984

[54] DIAGNOSTIC RADIOLOGY SYSTEM FOR ANGIOGRAPHIC X-RAY EXAMINATIONS

[75] Inventor: Rolf Pfeifer, Erlangen, Fed. Rep. of Germany

[73] Assignee: Siemens Aktiengesellschaft, Berlin & Munich, Fed. Rep. of Germany

[21] Appl. No.: 375,459

[22] Filed: May 6, 1982

[30] Foreign Application Priority Data

Jun. 3, 1981 [DE] Fed. Rep. of Germany ....... 3122098

[51] Int. Cl.$^3$ ................................................ A61B 6/00
[52] U.S. Cl. ..................................... 128/653; 358/111
[58] Field of Search ................................ 128/653–655; 358/111

[56] References Cited

U.S. PATENT DOCUMENTS 4,006,736  2/1977  Kranys et al. ....................... 128/655

FOREIGN PATENT DOCUMENTS 133388  11/1978  Japan .................................... 128/653

OTHER PUBLICATIONS

Ovitt, T. et al., "Development of a Digital Video Subtraction System for Intravenous Angiography", Proc.-Opt. Instrum. Eng. (U.S.A.) (1979) pp. 73–76.
Ovitt, T. W. et al., "The Development of a Digital Video Subtraction System for IV Angiography", Non-Invas. CV Measurements Conf.: Stanford, Calif., U.S.A. (Sep. 1978) pp. 61–65.
Brennecke et al., "Digital Processing of Videoangeographic Image Series Using a Minicomputer", IEEE Catalog No. 76CH1160–1C, 1976, pp. 255–260.

Primary Examiner—Kyle L. Howell
Assistant Examiner—Francis J. Jaworski
Attorney, Agent, or Firm—Hill, Van Santen, Steadman & Simpson

[57] ABSTRACT

An exemplary embodiment includes an image intensifier television chain and an image subtraction device connected thereto, with at least one image memory whose stored image data is subtracted from image data which occurs at other time than the stored image data, and a display device for the subtraction images. A central control console is present at which a display configuration representing individual stages of the examination sequence is provided, which display configuration is controlled by a central control device in such a manner that the respective examination stages are displayed. The display configuration can preferably be distributed along a graphical image suggestive of the chronological contrast medium progression.

3 Claims, 2 Drawing Figures

DIAGNOSTIC RADIOLOGY SYSTEM FOR ANGIOGRAPHIC X-RAY EXAMINATIONS

BACKGROUND OF THE INVENTION

The invention relates to a diagnostic radiology system for angiography x-ray examinations, comprising an image intensifier television chain and an image subtraction device connected thereto with at least one image memory whose image data is subtracted from image data which occurs at other times than the stored image data, and comprising a display unit for displaying the subtraction images, in which a control device for controlling image processing is present.

A diagnostic radiology system of this type is described for example, in an article from the conference publication IEEE Catalog No. 76CH 1160-1C, 1976, pages 255-260. This article relates to enhancement of an angiocardiographic image-series by digital processing methods. It is possible here to store in the image memory one radiograph, or image data based on several integrated radiographs which represents a contrast-medium-free cardiovascular image of the radiography subject, and to form a difference image from this stored image data and later image data which corresponds to the same region of the radiography subject after an x-ray contrast agent is introduced into the blood vessels. In this manner, a fluoroscopic image can be obtained in real time which shows only the blood vessels important for the diagnosis which are filled with contrast medium. It is also possible to record the image scene to be examined with the aid of a video recorder and to conduct the image subtraction on the basis of the recorded scene.

SUMMARY OF THE INVENTION

The object of the invention resides in designing a diagnostic radiology system of the type initially cited in such a fashion that a simple and clear, readily overseeable operation, in particular, image selection is possible.

In accordance with the invention, this object is achieved in that a central operating console is present on which display means for representing individual stages of the examination sequence are provided, which display means are connected to a control device and are controlled by the latter in such a manner that they display the respective examination stage. In the case of the inventive diagnostic radiology system, the respective examination stage is visually recognizable on the operating console, so that, for example, it can be checked in a simple manner which stage of an overall examination operation has been respectively attained and the following stage can be initiated. Thus it is, for example, readily possible, following display of the switching-on of fluoroscopy (by manual actuation of a key), to initiate a contrast medium injection, to subsequently effect the storage of a pre-filling (contrast-medium-free) image, then to trigger the storage of a filling image (blood vessels filled with contrast medium) in an additional image memory, and to finally terminate the examination sequence. The filling image is electronically subtracted from the pre-filling (contrast-medium-free) image, and the difference image is displayed on a monitor.

A particularly clear operation is achieved if the operating console bears a graphical image suggestive of the chronological contrast medium progression and the display means are disposed at successive associated locations therealong. This display configuration together with the graphical image accordingly indicates the respectively attained examination stage of an overall examination sequence.

The invention shall be explained in greater detail in the following on the basis of an exemplary embodiment illustrated on the accompanying drawing sheets; and other objects, features and advantages will be apparent from this detailed disclosure and from the appended claims.

DETAILED DESCRIPTION

Figure 1:
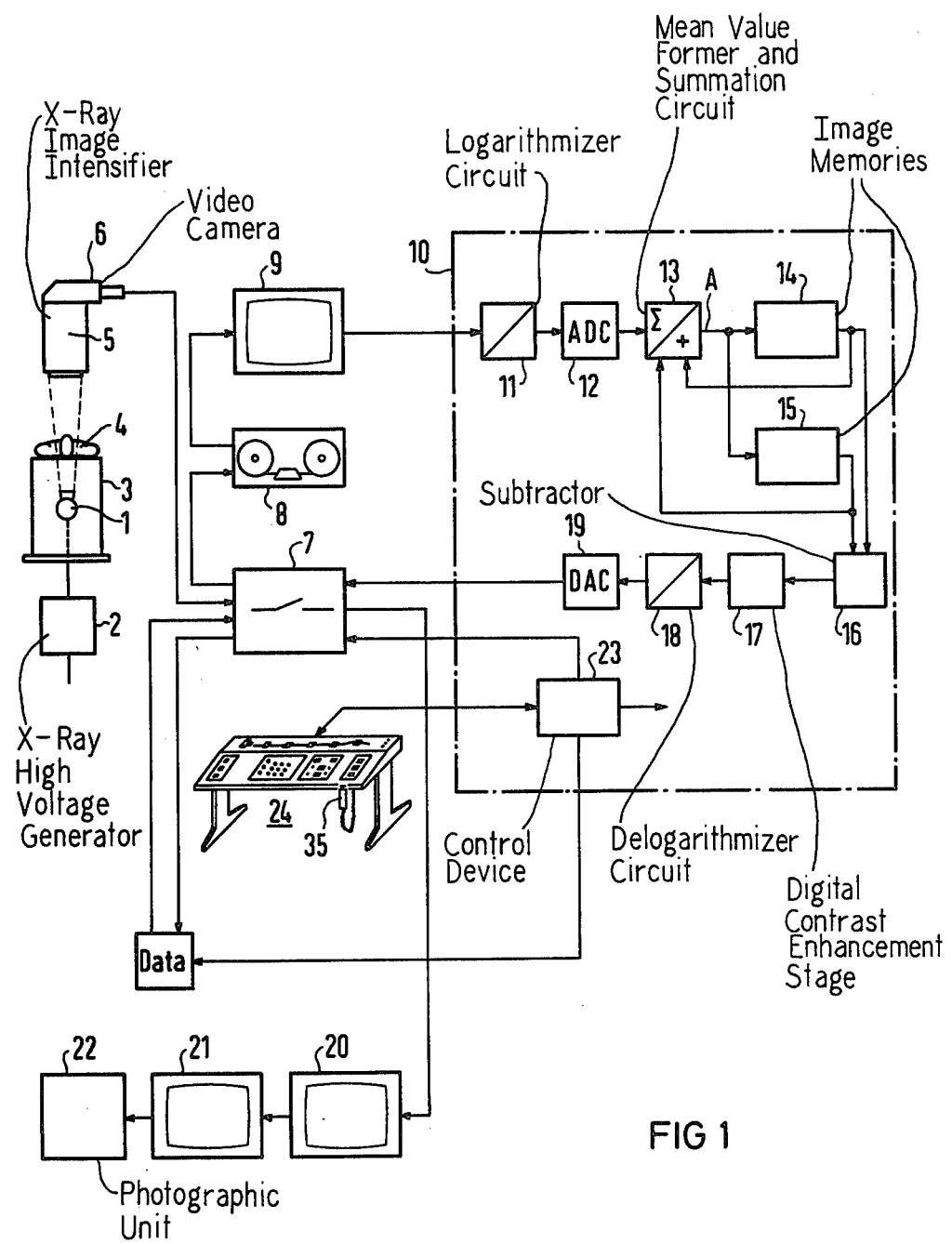
FIG. 1 illustrates a block representation of a diagnostic radiology system according to the invention.

In FIG. 1 an x-ray tube 1 is illustrated which is supplied by an x-ray generator 2 and irradiates a patient 4 lying on a patient support 3. An x-ray image intensifier 5 produces an intensified optical image, and a video camera 6 converts to the intensified optical image into a video signal which is supplied to a video distributor 7. The video distributor 7 controls the recording of the radiographs on a video recorder 8 and the display of these images on a monitor 9.

For the formation of difference images, either a video signal supplied in real time or a stored video signal delivered by the video subtraction device 10 is processed. The subtraction device 10 has at its input a logarithmizer 11 whose output signal is supplied to an analog-to-digital convertor 12. The logarithmizer 11 causes signals to be subtracted from one another which are proportional to the sum of the products of the mass attenuation coefficient and mass of all substances which lie in the ray path. Connected with the output of the analog-to-digital convertor 12 is a mean value formation unit 13 which effects a sliding, weighted mean value formation for the purpose of signal-to-noise ratio improvement. A summation of image signals can also take place. The thus obtained image signals are stored in two image memories 14 and 15 which are connected to a subtractor 16 whose output signal is supplied to the video distributor 7 via a digital contrast enhancement stage 17, a delogarithmizer 18, and a digital-to-analog convertor 19. The video distributor 7 may supply the subtraction image in analog form to monitors 20 and 21 for immediate display thereof. The subtraction image can be permanently retained with the aid of an image recording device 22, e.g., photographed.

For the production of angiography subtraction images, after initiation of the injection of a contrast medium in a blood vessel, before the contrast medium has spread in the vessel region to be examined, a masking signal is placed in the image memory 14 which masking signal corresponds to several contrast-medium-free images. The averaged, or the integrated data corresponding to the contrast-medium-free images is stored in the image memory 14. Subsequently, if possible during the maximum contrast medium filling of the vessel region to be examined, an averaging or integration, respectively, of several video images is effected and the data corresponding to these filling images is stored in the image memory 15. If the contents of the memories 14 and 15 are subtracted from one another by the subtractor 16, then subtraction images can be displayed on the monitors 20 and 21 which show only the vessel filled with contrast medium, but which no longer contain the background which is always the same.

For controlling the entire diagnostic radiology system a control device 23 is present which is activated by an operating console 24. The operating console 24 is illustrated in greater detail in FIG. 2.

Figure 2:
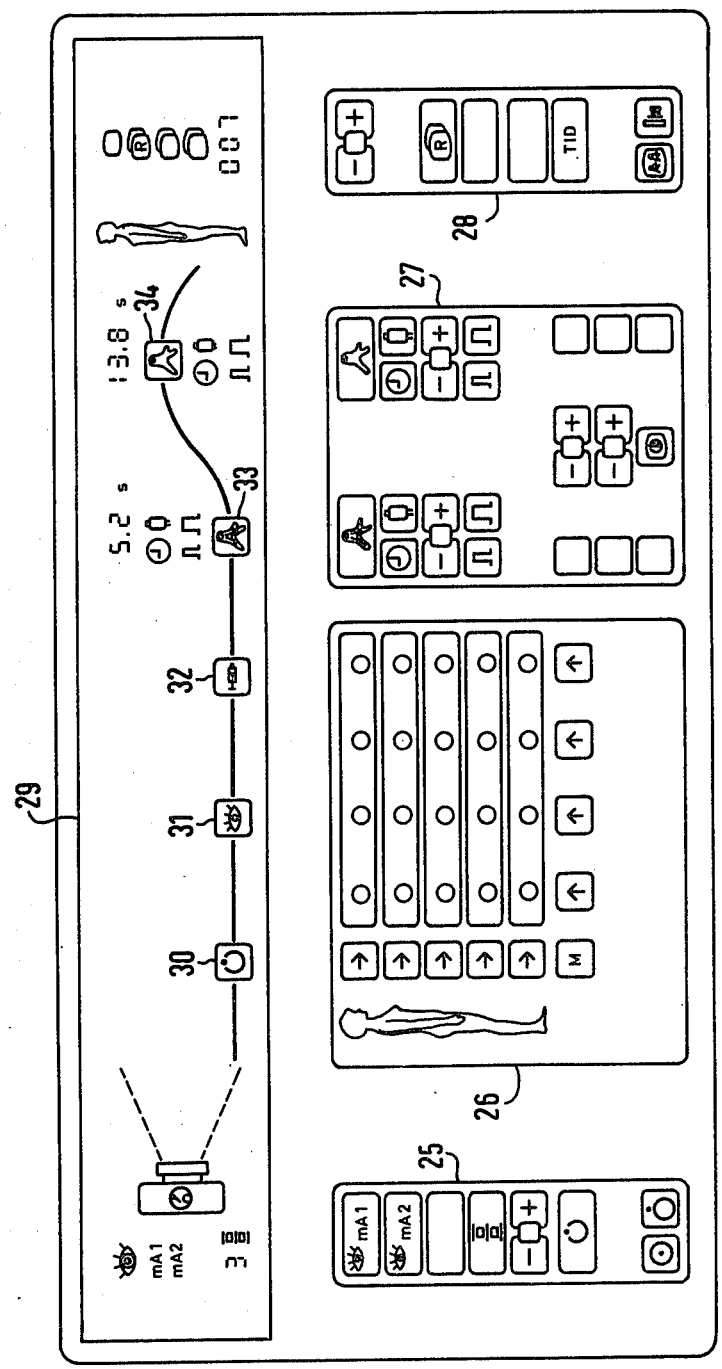
FIG. 2 illustrates the operating surface of the operating console of the diagnostic radiology system according to FIG. 1.

From FIG. 2 it is apparent that the operating surface of the operating console 24 exhibits four areas 25 through 28 in which keys (or buttons) are arranged. In the area 25, keys are arranged which serve the purpose of selection of the exposure values; in the area 27, keys are arranged which serve the purpose of controlling the examination sequence; in the area 28, keys are arranged which serve the purpose of controlling the image recording; and in the area 26, keys are arranged which make it possible to permanently retain specific values selected in the areas 25, 27, 29, i.e., which makes it possible to program dependently upon body region (organ) and examination type. Above the areas 25–28 a display field 29 is arranged which provides a schematic illustration suggestive of the contrast medium progression in a blood vessel. In the display field 29 namely, along the graphical image line suggestive of contrast medium progression, display means 30–34 for the individual stages of the examination sequence are provided which are connected to the control device 23, FIG. 1, which also controls the x-ray generator 2. The display means 30–34 are controlled by the control device 23 of FIG. 1, in such a manner that they display the respective examination stage. Each of the display means 30–34 is here disposed at the location of a graphical symbol which symbol graphically conveys the respective examination stage. Accordingly, the display means 30–34 are successively switched on to successively illuminate the respective associated graphical symbols. Through the display means 30 the graphical symbol indicating preparation of the diagnostic radiology system for providing a subtraction image is illuminated; through the display means 31, the graphical symbol representing the switching-on of fluoroscopy is illuminated; through the display means 32, the graphical symbol representing contrast medium injection is illuminated; through the display means 33, the graphical symbol representing the storage of a contrast-medium-free image in the image memory 14 (mask) is illuminated; and through the display means 34, the graphical symbol representing the storing of a filling image in the image memory 15 is illuminated. This input storage is selected with the aid of keys in the area 27 associated with a corresponding graphical symbol and proceeds through actuation of a trigger device 35 (FIG. 1) on the operating console 24.

FIG. 2 shows that the operating console combines all operating elements, necessary for the adjustment and control of the diagnostic radiology system, in a clear readily overseeable manner, so that a particularly simple and clear operation is possible.

In the exemplary embodiment of a diagnostic x-ray system for angiography x-ray examinations illustrated in FIG. 1, two image memories 14 and 15 are provided. In the image memory 15 an image is stored which occurs at a different time than the image that is stored in the image memory 14 in the form of a mask. It is also possible to dispense with the image memory 15 if the respective current video signal is subtracted from the image data stored in the image memory 14, and the resultant difference is then stored in the image memory 14.

It will be apparent that many modifications and variations may be made without departing from the scope of the teachings and concepts of the present invention.

Supplementary Discussion

A more detailed explanation of an angiographic system is found in an article entitled "Computer Angiography—Intravenous Arteriography" published in the English Edition of *Electromedica*, No. 2/1981 at pages 122 through 131, and this article is incorporated herein by reference by way of background.

I claim as my invention:

1. A diagnostic radiology system for angiography x-ray examinations, comprising an image intensifier television chain, an image subtraction device, connected thereto, including at least one image memory for storing image data which is subtracted from image data which occurs at other times than the stored image data to provide subtraction images, a display device for displaying the subtraction images, and a control device for controlling image processing, a central operating console is present having display means for representing successive individual stages of an angiographic examination sequence, which display means are connected to the control device and are controlled by the latter in such a fashion that they display the respective examination stage of said examination sequence.

2. A diagnostic radiology system according to claim 1, wherein the operating console has an elongated graphical image suggestive of the chronological contrast medium progression and the display means representing successive individual stages of the examination sequence are disposed at successive spatially offset locations along said elongated graphical image.

3. A diagnostic radiology system according to claim 2 with said display means of said central operating console representing at successive spatially offset locations along said elongated graphical image the respective individual stages comprising contrast agent injection, the storage of a contrast-medium-free image, and the storing of a filling image after the contrast medium has been introduced into the region under examination, such that said display means graphically represents the flow of contrast medium during the course of an angiographic x-ray examination.

* * * * *